United States Patent
Petersen et al.

(10) Patent No.: US 12,290,452 B2
(45) Date of Patent: *May 6, 2025

(54) MEASURING EQUIPMENT FOR USE IN CONNECTION WITH HIP PROSTHESIS SURGERY

(71) Applicant: MEDICHANICAL ENGINEERING APS, Vejle (DK)

(72) Inventors: Eske Winther Petersen, Aalborg (DK); Poul Torben Nielsen, Aalborg (DK)

(73) Assignee: MEDICHANICAL ENGINEERING APS, Vejle (DK)

( * ) Notice: Subject to any disclaimer, the term of this patent is extended or adjusted under 35 U.S.C. 154(b) by 23 days.

This patent is subject to a terminal disclaimer.

(21) Appl. No.: 17/930,575

(22) Filed: Sep. 8, 2022

(65) Prior Publication Data

US 2023/0009959 A1 Jan. 12, 2023

Related U.S. Application Data

(63) Continuation of application No. 16/612,657, filed as application No. PCT/EP2018/064376 on May 31, 2018, now Pat. No. 11,439,518.

(30) Foreign Application Priority Data

May 31, 2017 (SE) .................... 1750690-8

(51) Int. Cl.
*A61F 2/46* (2006.01)
*A61F 2/34* (2006.01)
*A61F 2/30* (2006.01)

(52) U.S. Cl.
CPC .............. *A61F 2/4657* (2013.01); *A61F 2/34* (2013.01); *A61F 2002/30242* (2013.01); *A61F 2002/30579* (2013.01); *A61F 2002/4666* (2013.01)

(58) Field of Classification Search
CPC .. A61F 2/4657; A61F 2002/4659; A61F 2/34; A61F 2002/3483; A61F 2002/30242; A61F 2002/30579; A61B 5/4571
See application file for complete search history.

(56) References Cited

U.S. PATENT DOCUMENTS

| 4,987,904 A | 1/1991 | Wilson |
| 5,141,512 A | 8/1992 | Farmer et al. |

(Continued)

FOREIGN PATENT DOCUMENTS

| EP | 0860143 A2 | 8/1998 |
| EP | 1555939 | 4/2004 |

(Continued)

OTHER PUBLICATIONS

International Search Report for PCT/EP2018/064376 mailed Sep. 7, 2018.

(Continued)

*Primary Examiner* — Anu Ramana
(74) *Attorney, Agent, or Firm* — Sandberg Phoenix & von Gontard P.C.

(57) ABSTRACT

A measuring adapter for a measuring instrument for use in connection with hip prosthesis surgery comprises a measuring head and a connector. The measuring head comprises a front end, a rear end and convex upper surface and is divided into at least two separate sections. The measuring head comprises an axially extending central through-going bore adapted to receive an actuating rod. The measuring head is expandable from a relaxed state to an expanded state by axially displacing the actuating rod in the central through-going bore. The connector is hollow and divided at one end in axial direction of the measuring head into a number of legs corresponding to the number of separate sections of the measuring head; each leg being connected to one of the sections of the measuring head. At least a part of the upper (Continued)

surface of the measuring head is adapted, when in the expanded state, to adopt the shape of a spherical cap or a convex shape comprising at least a spherical segment.

17 Claims, 8 Drawing Sheets

(56) References Cited

U.S. PATENT DOCUMENTS

| | | | |
|---|---|---|---|
| 5,725,593 A * | 3/1998 | Caracciolo | A61F 2/3603 623/22.23 |
| 5,779,710 A | 7/1998 | Matsen, III | |
| 7,331,965 B2 | 2/2008 | Nielsen | |
| 10,507,029 B2 | 12/2019 | Meridew et al. | |
| 2004/0059340 A1 * | 3/2004 | Serra | A61F 2/4684 606/102 |
| 2005/0171614 A1 | 8/2005 | Bacon | |
| 2009/0048603 A1 * | 2/2009 | Hoag | A61F 2/30724 606/89 |

FOREIGN PATENT DOCUMENTS

| | | |
|---|---|---|
| FR | 2684287 A1 | 6/1993 |
| WO | 2004034904 A1 | 4/2004 |
| WO | 2005003680 A1 | 1/2005 |
| WO | 2008035198 A2 | 3/2008 |
| WO | 2008080061 A1 | 7/2008 |

OTHER PUBLICATIONS

Written Opinion for PCT/EP2018/064376 mailed Sep. 7, 2018.
Search Report and Office Action from corresponding Swedish Application No. 1750690-8 dated Dec. 12, 2017.

* cited by examiner

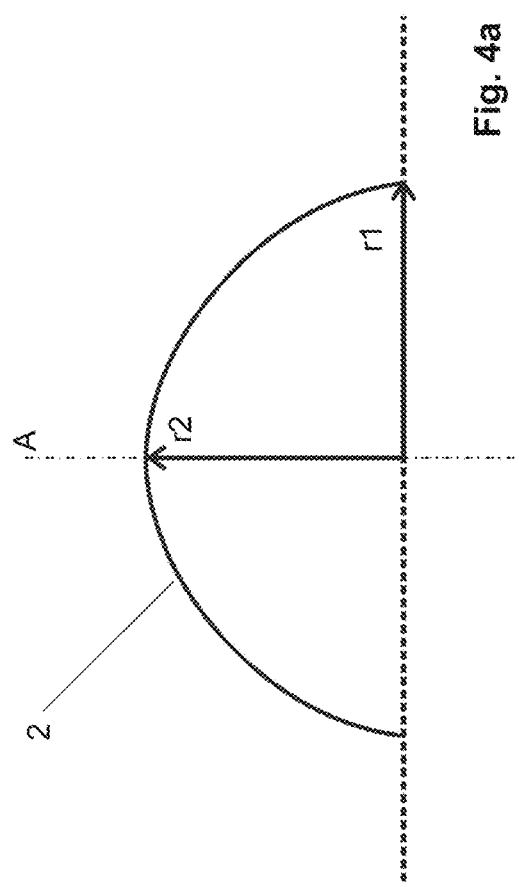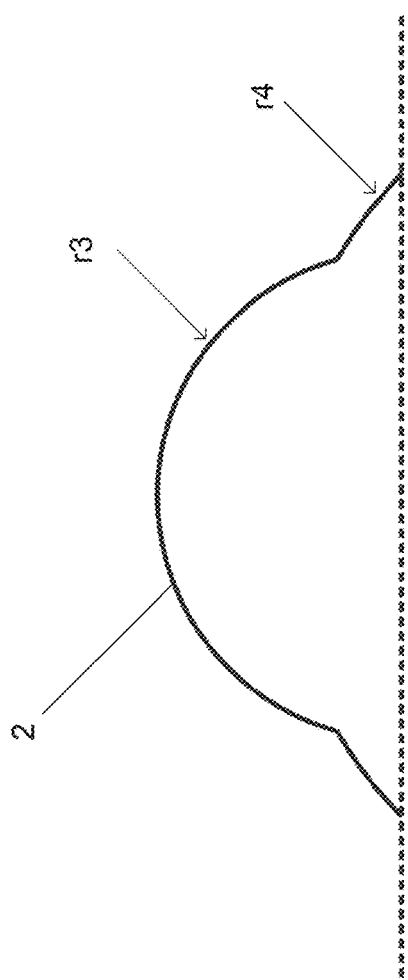

MEASURING EQUIPMENT FOR USE IN CONNECTION WITH HIP PROSTHESIS SURGERY

CROSS-REFERENCE TO RELATED APPLICATIONS

This application is a continuation of application Ser. No. 16/612,657 filed 11 Nov. 2019, now U.S. patent Ser. No. 11/439,518, which in turn is the US National Stage under 35 USC § 371 of International Application No. PCT/EP2018/064376, filed 31 May 2018 which claims priority to Swedish Application No. 1750690-8 filed 31 May 2017, all of which are incorporated herein by reference.

TECHNICAL FIELD

A measuring adapter is disclosed, for use in connection with hip prosthesis surgery.

BACKGROUND

Today, implantation of artificial hip joints is a standard procedure in surgery. Hip joint replacement eliminates pain and restores the function of the hip joint. The number of such operations is expected to increase in the future, due to a larger elderly population and the importance of being physically active even in advanced age.

During the last 35-40, years bone cement has been used for anchoring prosthesis components when inserting artificial hip joints. Good results have been achieved with this technique, but after long time observation of large groups of patients, problems have been detected with loosening of the inserted prosthesis component. Furthermore, a considerable bone loss has occurred around the prosthesis component so that replacement surgery is difficult.

Alternative techniques such as uncemented sockets, where the socket is anchored in acetabulum (the pelvic cavity), have been developed. Different anchoring methods have also been developed, and the method appearing to provide good results on short as well as long term is the use of metal sockets, preferably made of materials such as, e.g., titanium or vitalium. These metal sockets are typically hemispherical with a porous surface, i.e. the surface is rough which provides the possibility of ingrowth of bone cells into the surface of the metal socket leading to an anchoring of the socket in the acetabulum. A supplementing hydroxapatite coating promotes the bone ingrowth process.

When inserting an uncemented metal socket with a porous surface, a hole, essentially hemispherical, fitting the metal socket to be inserted is milled in acetabulum. For example, if acetabulum is milled up to 60 mm, a 60 mm metal socket is inserted. Then the metal socket is anchored further with 2-4 screws through holes in the metal socket. However, screw anchoring has been shown to lead to adverse effects, since the polyethylene decomposition product from the liner (wear component) can migrate through the screw holes and out into the bone, and here produce osteolysis or necrosis of the bone.

In order to avoid these adverse effects, another anchoring method, a so-called "press-fit"-technique, has been developed, where a hole, essentially hemispherical, is milled in acetabulum, wherein the hole is up to approximately 75 mm in diameter, and a metal socket somewhat larger in diameter subsequently is inserted. A great tension is thereby achieved between bone and metal socket, whereby the metal socket is held in place without the need of screws. In the course of the first weeks after the operation, the bone grows from the pelvis into the surface coating of the metal socket and ensures the so-called secondary anchoring.

The described technique is, however, rather demanding and requires an experienced physician to perform the hip prosthesis surgery, as there is risk of problems if the metal socket has not been correctly inserted. If the metal socket is not securely clamped, there is a risk that it may loosen in the course of the first days after the operation. If the metal socket is too strongly clamped, there is a substantial risk of fracture in the pelvis bone around the metal socket, whereby the implant becomes unstable.

Therefore, it is important to insert the right size of metal socket. In order to determine which size of metal socket to be used, previously a template or a test prosthesis has been used and placed in acetabulum and fixed by a light pressure in acetabulum, after which a metal socket in the same size or with 1-2 mm oversize is selected for implantation.

However, using a template or a test prosthesis is not a good and objective method of measuring the milled cavity and determining the size of the socket to be implanted, and one may risk to use/insert more than one metal socket in order to let it fit optimally. A great disadvantage by this method is that a metal socket that has been in contact with a patient cannot be autoclaved and used for another patient. This metal socket has to be discarded, which also implies increased costs in connection with a hip prosthesis surgery.

Patent publications FR 2 684 287 and U.S. Pat. No. 5,141,512 describe equipment for measuring in connection with placing of a hip socket, but not decidedly measuring the size of the milled hole and the elasticity of acetabulum.

In EP 1 555 939 a measuring instrument is described which can be used to measure/register the size and elasticity as well as the shape of the acetabulum.

However, in the prior art measuring devices, it is not possible to assure the fitting of the template in the milled cavity, unless along the outer lateral diameter of the template, and also there is a mismatch between the shape of the template and the final prosthetic sphere.

An object is to overcome these problems.

SUMMARY

Briefly stated, disclosed is a measuring adapter (1) for a measuring instrument for use in connection with hip prosthesis surgery, wherein the measuring adapter (1) comprises a measuring head (2) and a connector (3); the measuring head (2) comprises a front end (2a), a rear end (2b) and an upper surface (4a); wherein the upper surface (4a) is convex; the measuring head (2), along an axial direction of the measuring adapter (1), further comprises a central through-going bore (5) adapted to receive an actuating rod (8); the measuring head (2) is adapted to expand from a relaxed state to an expanded state when the actuating rod (8) is axially displaced in the central through-going bore (5); and the measuring head (2) is divided into at least two separate sections (6); the connector (3) is hollow and slotted at one end in axial direction of the measuring head (2) into a number of legs (7), the number of legs (7) corresponding to the number of the at least two separate sections (6) of the measuring head (2); wherein the legs (7) of the connector (3) are each connected to one of the at least two separate sections (6) of the measuring head (2) on the rear end (2b) of the measuring head (2); and a securing arrangement (18) is provided at the opposite end of the connector (3) relative to the connection to the measuring head (2).

The measuring adapter has one relaxed state and may adopt several expanded states depending on the position of the actuating rod in the central through-going bore.

At least a part of the upper surface (4a) of the measuring head (2) is adapted to, in one expanded state, adopt the shape of a spherical cap; or a convex shape comprising at least a spherical segment.

Thus, a cross section, perpendicular to the axial direction of the connector (3), of the measuring head (2) in one expanded state defines a circle.

This is especially advantageous, since a cross section of the milled cavity is circle-shaped due to the milled cavity of the acetabulum being hemisperically shaped. Thus, a measuring head will fit into the milled cavity to a larger degree than measuring heads previously known in the art, which do not adopt a spherical cap or a convex shape comprising at least a spherical segment in their expanded state, and which thus do not have a cross section, perpendicular to the axial direction of the connector (3), of the measuring head (2), which, in one expanded state, defines a circle.

In other words, a part of the outline of a cross section of the measuring head (2), along an axis (A) along the axial direction of the connector (3) is adapted to, in one expanded state, adopt a curve defined by an arc of a circle.

According to one embodiment, the measuring head (2) is adapted to, in one expanded state, adopt the shape of a largely hemispherical surface (4c). One advantage of such a measuring head is that it will fit almost perfectly in a hemispherical cavity milled in the acetabulum.

According to another embodiment, the measuring head (2) in the relaxed state has the surface of a collapsed hemisphere; the surface of a collapsed spherical cap; or a convex shape comprising at least a collapsed spherical segment. This is to be understood as the measuring head's circumference diameter will have to be expanded in order for the elements of the measuring head to align with a hemisphere, a spherical cap; or a convex shape comprising at least a spherical segment, respectively. The purpose is to determine a diameter where parts of the measuring head's periphery, curved with the same radius, aligns with a part of the periphery of a hemisphere with such a radius. Thus, the "ideal" shape at e.g. +2 mm from the initial collapsed (i.e. relaxed) position may be determined. In the ideal shape every transversal cross section through the measuring head will be a circle. This means that every transversal cross section through the positively curved outer surface (4a, 4c) forms a circle.

According to yet another embodiment, the measuring head (2) is described by a width (w) and a height (h); wherein the width is the ideal width (w) of the measuring head (2) perpendicular to the axial direction of the connector (3), and the height (h) is the height of the measuring head (2) along the axial direction of the connector (3); and wherein $$h < \frac{w}{2}.$$

Thus, the height (h) of the measuring head (2) is less than half of the ideal width (w) of the measuring head (2). In other words, the radius at the equator is larger than the distance from the center point of the equatorial circle to the pole of the measuring head's periphery.

One advantage of such a measuring adapter is that such an adapter will be less likely to push itself out of the acetabulum if the cavity is not deep enough, as may sometimes be the case if an implant socket is used that is of similar geometry.

According to one embodiment, the measuring head (2) in the relaxed state is collapsed compared to a perfect hemisphere and adapted to, in one expanded state, adopt the shape of a largely hemispherical surface (4c). This is to be understood as the measuring head's circumference diameter will have to be expanded in order for the elements of the measuring head to align with a hemisphere. The purpose is to determine a diameter where parts of the measuring head's periphery, curved with the same radius, aligns with the periphery of a hemisphere with such a radius. Thus, the "ideal" shape at e.g. +2 mm from the initial collapsed (i.e. relaxed) position may be determined.

According to one embodiment, the measuring head (2) is described by at least two radiuses r1 and r2; wherein r1 is the ideal radius of measuring head (2) perpendicular to the axial direction of the connector (3); r2 is the radius of the measuring head (2) as measured along the axial direction of the connector (3) from the intersection of an axis (A) along the axial direction of the connector (3) with the radius r1; and r2 is smaller than r1. When the measuring head's circumference diameter is expanded, the elements of the measuring head align with parts of at least two hemispheres. One advantage is that such an adapter can provide a precise measurement of stability similar to implant sockets with dual (or multi) radiuses.

According to another embodiment, the measuring head (2) in the relaxed state has a convex shape comprising at least a collapsed spherical segment.

According to another embodiment, the measuring head (2) comprises windows or through-going holes (10). One advantage of such an adapter head is that, through these holes, the surgeon is able to see whether the measuring head is pushing itself out of the pelvic cavity (acetabulum) when being expanded. Thus, the surgeon can correctly determine the size of the milled cavity of the acetabulum, since when the measuring head (2) begins pushing itself out of the acetabulum, the correct size has been exceeded or the cavity has not been milled deep enough. Hence, in addition to determine the size of the milled cavity of the acetabulum, the surgeon is also able to observe movements of the measuring head (2) in the cavity caused by the expansion of the measuring head (2).

Another advantage is that the weight of the adapter is reduced.

The windows may be made of transparent polymer.

According to yet another embodiment, wherein the measuring head (2) is divided into at least three separate sections (6). This division is made in order to achieve a satisfactory contact of the surface of the measuring head against the acetabulum, particularly when the measuring head is in an expanded state after expansion of the measuring head.

These sections are connected to the legs of the connector, which are provided at the end of the connector facing the measuring head and being slotted in axial direction. The slotting enables the connector to absorb the forces coming from the measuring head when it expands.

According to another embodiment, at least a part of the upper surface (4a) of the measuring head (2) comprises a rough surface.

According to another embodiment, the upper surface (4a) of the measuring head (2) of the measuring adapter (1) comprises a rough surface (4a') at the lower part of the upper surface (4a) and a smooth surface (4a") on the upper part of the upper surface (4a). This ensures that the measuring head of the adapter can be correctly placed in the acetabulum and that the right diameter of the acetabulum is measured. The rough surface provides for better engagement of the measuring head with the spherical surface of the grooved/milled bone tissue of the acetabulum. When using a measuring instrument, the measuring head is placed against the edge of the acetabulum, whereby the rough surface prevents displacing of the measuring head during expansion of the measuring head.

Both the bottom part 4a' and the top part 4a" may have a rough surface.

The bottom part 4a' may have a rougher surface than the top part 4a".

The entire measuring head may have a rough surface.

The rough surface may be provided with different patterns which can be an arbitrary number of strings, linear and/or crossing flutes and/or beads.

The rough surface may comprise protrusions having a height between 0.1 and 3 mm and a diameter between 0.1 and 10 mm.

The protrusions may be cylinder-shaped.

The protrusions may be cone-shaped.

The protrusions may be spikes having a circular, triangular, square or pentagonal cross-section or having a cross-section with any number of sides.

Since only a few acetabuli have largely hemispherical shape, it is not necessary that the entire surface of the measuring head has a rough surface. Therefore a part of the surface of the measuring head may be provided with a smooth surface, since a smooth surface will be easier to keep clean and thereby more hygienic.

According to one embodiment, the securing arrangement (18) comprises recesses for a bayonet socket. When the securing arrangement (18) of the adapter are recesses for a bayonet socket, a mounting ring of the measuring unit, to which the adapter is to be secured, comprises means for engaging the securing arrangement (18) of the adapter which are designed as pins for a bayonet engagement.

By using a bayonet engagement it is possible to readily assemble the adapter with a measuring unit. Furthermore, a bayonet engagement is not a difficult assembly to manufacture, irrespectively whether the adapter is cast in one piece or the connector of the adapter is a pipe. Also, it is specifically advantageous when a rotational displacement is used, since rotation into a relaxed state of the measuring head also may release the bayonet engagement.

Alternative embodiments for the securing arrangement between the adapter and a measuring unit may e.g. be: a screw thread providing a very stable assembly, but having the drawback that it may be difficult to clean; a snap lock performing a releasable engagement when the adapter is placed in a measuring unit, implying easy and quick replacement of an adapter, but having the drawback that they may be worn out and thereby cannot hold the adapter in the measuring unit.

According to another embodiment, the measuring adapter (1) is made of a hard yet flexible material, wherein the material is chosen from the group consisting of a metal alloy, a plastic material, a plastic composite, a ceramic material and combinations thereof. Use of such a material ensures that the measuring head of the adapter is able to expand and that the adapter is easy and inexpensive to manufacture.

For example, the adapter may be made of a hard yet flexible plastic composite, such as polyoxymethylene POM or the like. By making the adapter of a plastic composite, the adapter may either be molded in the same way as when making an adapter of a metal alloy, or it may be rotationally molded, where the subsequent processing of making of slots and recesses may readily be performed afterwards.

It is advantageous that all materials are heat resistant, so that regardless of the material the adapter is made of, it is possible to autoclave the measuring adapter.

It will be an advantage to avoid joints in the adapter and, if the adapter is made of a metal alloy, that the adapter is made in one piece where the adapter is either cast with cutouts and recesses, or that they are made subsequently. Furthermore, the metal must have a certain temperature resistance as an adapter made in a metal alloy will be an expensive equipment. Such an adapter will be used many times and is therefore autoclaved after each use.

According to one embodiment, the central through-going bore (5) is conical.

Alternatively, the central through-going bore may be largely conical.

Alternatively, the central through-going bore may be a straight bore.

Alternatively, the central through-going bore may have curved faces.

According to another embodiment, the diameter of the measuring head (2) in the relaxed state is from 42 to 85 mm, preferably from 50 mm to 70 mm.

According to yet another embodiment, the diameter of the measuring head (2) in the expanded state is up to 4 mm larger than the diameter of the measuring head (2) in the relaxed state. Thus, in the expanded state, the diameter of the measuring head is from 46 to 89 mm, preferably from 54 to 74 mm. A greater expansion of the diameter of the measuring head than 4 mm may cause a fracture in acetabulum, whereby the implant becomes unstable.

According to a second aspect, a measuring adapter (1) for a measuring instrument for use in connection with hip prosthesis surgery is also provided. The measuring adapter (1) comprises a measuring head (2) and a connector (3); and the measuring head (2) comprises a front end (2a), a rear end (2b) and an upper surface (4a); wherein the upper surface (4a) is convex; the measuring head (2), along an axial direction of the measuring adapter (1), further comprises a central through-going bore (5) adapted to receive an actuating rod (8); the measuring head (2) is adapted to expand from a relaxed state to an expanded state when the actuating rod (8) is axially displaced in the central through-going bore (5); and the measuring head (2) is divided into at least two separate sections (6). The connector (3) is hollow and slotted at one end in axial direction of the measuring head (2) into a number of legs (7), the number of legs (7) corresponding to the number of the at least two separate sections (6) of the measuring head (2); wherein the legs (7) of the connector (3) are each connected to one of the at least two separate sections (6) of the measuring head (2) on the rear end (2b) of the measuring head (2); and a securing arrangement (18) is provided at the opposite end of the connector (3) relative to the connection to the measuring head (2). The measuring head (2) comprises windows or through-going holes (10) or windows.

A measuring adapter can be used to in a simple way measure/register the size and the elasticity as well as the shape of acetabulum. Importantly, in the relaxed state, the surface of the measuring head does not define a hemisphere. Rather, the surface of the measuring head may define a flattened hemisphere or a collapsed hemisphere.

However, in an expanded state, the surface of the measuring head defines a substantially hemispherical surface or parts of a substantially hemispherical surface. Thus, in an expanded state, the shape of the measuring head is essentially hemispherical; defines at least one essentially hemispherical cap or partly defines at least one essentially spherical segment. Since the acetabulum is milled with a hemispherical drill and since the socket to be inserted also defines the surface of a hemispheric, a more accurate measurement of the cavity and determination of the socket to be implanted can be achieved by using a measuring adapter having a measuring head. A measuring instrument will also make it easy and simple to measure the diameter of an acetabulum by a hip operation. Hence, the use of a measuring adapter may lead to hip prosthesis operations becoming safer since the risk of choosing a metal socket which is too small or too large for the milled cavity in the acetabulum is reduced. In addition, the costs of such operations are reduced.

Through the windows or through-going holes (10), the surgeon is able to observe the surface of the cavity and how well the measuring head (2) fits into the cavity. In addition, movements (such as the measuring head pushing itself out of the pelvic cavity (acetabulum) when being expanded by the displacement of the actuation rod (8) may also be observed and the alignment of the measuring head (2) with the milled cavity can be observed. Thus, the correct size of the milled cavity may be determined.

According to a third aspect, a measuring instrument (11) is also provided, comprising a measuring adapter (1) according to any one of the variations described above and a measuring unit (12) comprising an actuating rod (8) adapted to be received by the central through-going bore (5) of the measuring adapter (1), wherein a main part of the actuating rod (8) is adapted to interact displaceably axially with the central through-going bore (5) of the measuring adapter (1) and thereby change the diameter of the measuring head (1), the measuring unit (12) further comprising a mounting ring comprising means for engaging the securing arrangement (18) of the measuring adapter (1), wherein the mounting ring is connected with a handle means, wherein, in connection with the handle means, means for axial displacement of the actuation rod (8) and registration of the relative displacement of the actuation rod (8) relative to the measuring head (2) is provided.

The measuring unit may be made of the same or of a different material as the measuring adapter. It is advantageous that all materials are heat resistant, so that regardless of the material the adapter (and the measuring unit) is made of, it is possible to autoclave the measuring adapter, the measuring unit or entire measuring instrument.

If the measuring instrument is made of a sufficiently inexpensive material, the adapter and the measuring unit may be made in one piece. Thus, for each hip operation, a series of measuring instruments with different diameter of the measuring head are to be used. Following use, the used measuring instruments are to be discarded or autoclaved.

Before inserting a metal socket in acetabulum, the measuring instrument is used to measure the cavity of the acetabulum into which the socket is to be implanted. A measuring adapter having a measuring head with a desired diameter is coupled to the measuring unit by means of the coupling arrangement and the mounting ring. The measuring head of the adapter is inserted into the acetabulum so that the lower edge of the measuring head fits with the inner circumferential rim of the acetabulum. By actuating the handle means for axial displacing the actuation rod, the actuation rod will perform an axial displacement towards the measuring head and the main part of the actuation rod will interact with the central through-going bore of the measuring head and thereby force the separate sections of the measuring head outwards. Spreading of the separate sections of the measuring head will cause the diameter of the measuring head to expand and, importantly, will cause the surface of the expanded measuring head to define a substantially hemispherical surface, whereby the measuring head is clamped in the acetabulum. At a certain pretension, the diameter of the measuring head is read.

Optionally, a depth gauge is used for measuring the possible distance from the surface of the front end of the measuring head and down into the bottom of the acetabulum. Such a distance may occur if the measuring head is not fully expanded and thus has not adopted the shape of a hemisphere which fits into the milled hemispherical cavity of the acetabulum. This may also happen if the milled cavity is not an essentially hemispherical cavity.

After measuring of the diameter, and optionally the depth of the acetabulum, the handle means are actuated for axial displacement of the actuation rod so that the actuation rod performs an axial displacement in towards the handle, and the measuring head returns to the relaxed state and can be removed from the acetabulum.

In order for the measuring head of the adapter to expand by an axial movement of the actuation rod, a part of the actuation rod will interact with a face and/or an edge of the central through-going bore inside the measuring head of the adapter. Preferably, the part of the actuation rod, which is adapted to interact with the face and/or edge of the central through-going bore inside the measuring head of the adapter, is conical.

In neutral position of the actuation rod the at least two, such as three, separate sections of the measuring head are largely gathered, i.e. the measuring head is in its relaxed position, and by axial displacement of the actuation rod, the at least two separate sections of the measuring head will be pressed away from each other, and the diameter of the measuring head will expand with up to 4 mm and, importantly, the measuring head will adopt an essentially hemispherical form. A greater expansion of the diameter of the measuring head than 4 mm may cause fracture in acetabulum.

The central through-going bore in the axial direction of the measuring adapter enables passing the actuation rod through the connector, up inside and out through the measuring head. Preferably, as described above, the central through-going bore in the measuring head is conical.

In one embodiment, a main part of the actuation rod is located in the central through-going bore of the measuring head.

In one embodiment the through-going bore in the measuring head is a straight bore and a main part of the actuation rod is largely conical or ball-shaped, whereby the main part of the actuation rod interacts with a rim part of the through-going bore in the measuring head.

Alternatively, the through-going bore in the measuring head is largely conical or with curved faces and a main part of the actuation rod is a rod with increased diameter in relation to the actuation rod itself, whereby the upper edge section of the main part of the actuation rod interacts with surfaces of the through-going bore in the measuring head.

In another embodiment, the through-going bore in the measuring head is largely conically or with curved faces, and the main part of the actuation rod is largely conical or spherical, whereby surfaces of the main part of the actuation rod interacts with surfaces of the through-going bore in the measuring head.

In the two first alternatives, it will be necessary to safeguard the faces of either the through-going bore in the measuring head or the main part of the actuation rod, as they are to interact with an edge section of the opposing part. By repeated actuation of the actuation rod, wear may occur where the edge section hits the opposing surface. A safety measure may be surface coating of the exposed surfaces, or by making the measuring head and the main part of the actuation rod of materials with different hardness, so that the item with the edge part is made of the softest material.

The means for axial displacement of the actuation rod may be a millimeter screw device. Such a millimeter screw device will enable placing the measuring head of the adapter in an acetabulum, make it fit and thus, without further actuation in axial direction, enable screwing on the millimeter screw device so that the actuation rod is displaced axially into the measuring head bore, and thereby increasing the diameter of the measuring head.

Such a millimeter screw device may include a spring in connection with an adjustment part and a swivel ring with one or more measuring indicators. Furthermore, it may also be a ratchet function inside the millimeter screw device.

In one embodiment, the millimeter screw device is designed so that it may "click over" (overload protection) in order to avoid too much expansion of the measuring head, and too strong clamping of the measuring head in the acetabulum, thus avoiding fracture of the acetabulum.

The measuring indicators on the measuring ring and on the measuring unit provide that by counting turns of the swivel ring and by reading measuring units by means of a conversion factor, the increase of the diameter of the measuring head may be determined. An adjusting part is used every time a new adapter is inserted in the measuring instrument, whereby the measuring instrument is adjusted to neutral position.

In an alternative embodiment, the means for axial displacement of the actuation rod is chosen from the group consisting of hydraulics, pneumatic and/or electricity driving a motor or a unit that interacts with the actuation rod.

The axial displacement of the actuation rod may be motorized, enabling fine adjustment of the diameter of the measuring head in the acetabulum. Furthermore, it will not be the doctor's ability to adjust the measuring instrument, which is decisive for determining the socket size. Additionally, problems with holding the measuring head in the socket simultaneously with screwing or moving the actuation rod manually in axial displacement are avoided. This will make the measuring instrument lighter and the measurements more objective.

For measuring the actual displacement of the actuation rod, registration of the relative displacement of the actuation rod in relation to the measuring head is achieved by reading one or more measuring indications applied on the handle.

The measuring indicators are to be placed so that a user of the measuring instrument does not confuse the measurements read, which may cause a wrong metal socket to be pressed into the acetabulum, whereby problems such as bad fixation of the metal socket or fracture in acetabulum may arise.

In one embodiment, the measuring instrument is connected to a computer for controlling and/or registering the relative displacement of the actuation rod relative to the measuring head.

The measuring instrument may be used for collecting data on a computer connected thereto. The computer may be coupled to the motor or measuring unit and thereby measure the turns that correspond to a certain relative displacement. Alternatively, the computer may be coupled to a measuring arrangement which is capable of measuring, e.g. by means of optics, lasers or the like, the relative displacement of the actuation rod in relation to a fixed point in the measuring instrument.

A large data base may be generated from the data collected from several operations. Thus, an increasing amount of experience is collected as to how an acetabulum may be shaped. This will make it easier and quicker to find a socket fitting optimally within the acetabulum.

Furthermore, such a system with a computer for controlling and registering will be a good tool in teaching inexperienced/new physicians for hip/prosthesis operations as experiences from previous operations are stored in the database. This makes it possible for the doctors performing hip prosthesis surgery to benefit from experience and/or information collected from previous operations before they commence the operation.

In order to optimize the hip prosthesis operation, it is important for the doctors to measure the pressure to which the acetabulum will be subjected to at the insertion of the metal socket, as the pressure tolerated by the acetabulum most likely will be different with regard to different groups of patients. E.g. it may be difficult to achieve sufficient stability of the metal socket in patients with osteopsathyrosis.

The pressure exerted by the metal socket on acetabulum may be estimated simultaneously with measuring the diameter of acetabulum with a measuring instrument. The measuring instrument is provided with a pressure registering unit connected to the measuring head, so that simultaneously with registration of the increase of the diameter the pressure action of the measuring head on acetabulum is measured.

The pressure registration unit may e.g. be pressure transducers provided in or on the measuring head. The pressure registration unit must be durable and securely fastened as the measuring head is forced around in acetabulum in order to ensure selection of the correct metal socket.

Alternatively, piezo-electric crystals may be used for pressure registration on the measuring head.

By comparing pressure measurements, diameter of the metal socket and the patient's data, the doctors may reduce the problems with loose metal sockets and fracture of acetabulum. Such problems may lead to the patient needing to immediately undergo a new operation or to have a replacement operation earlier than expected.

In order to have a flexible system for measuring acetabulum during hip operation, the adapter for use in the measuring instrument is replaceable. Thus, the adapter and the measuring unit may be made of different materials.

Typically, an adapter will be made of a less expensive material than the measuring unit, whereby it is possible to practice a method where an adapter is used once and then discarded. This results in saving of autoclaving of an adapter after use. In addition, the risk of infection or other unwanted contamination is reduced.

Furthermore, by using a replaceable adapter it is possible to provide a series of adapters with different diameter of the measuring head, where the measuring head diameter in neutral position may vary from 42 to 85 mm, preferably between 50 and 70 mm.

It is advantageous to provide an adapter series where the measuring head has different diameter. The measuring instrument may thus be used for all types of hip operations by replacing the adapter. This means that a measuring instrument with adapter having a small measuring head may be used for persons undergoing pelvis operations where the acetabulum does not have a large diameter, whereas an adapter with large diameter is preferably used in pelvis operations where the acetabulum has a larger diameter.

A series of adapters with different diameters of the measuring head may be provided with diameters in steps of about 2 mm measured when the measuring head of the adapter is in the relaxed position and is not influenced by the actuation rod. However, as an example, the step size of the measuring head diameter of the adapter is to be maximum 3 mm if the diameter of the adapter measuring head can expand up to 4 mm.

This implies that the adapter, preferably, is not to be brought to an extreme position of its measuring range before an adapter having a greater measuring head diameter is used instead. Thereby, for an inexperienced and/or unskilled physician a rapid and more precise measurement of the diameter of the acetabulum is achieved.

Furthermore, it may be easier to find an adapter that almost fits into the acetabulum, after which the actual diameter of the acetabulum is achieved by fine adjustment of the measuring unit.

Furthermore, for adapters made of a more expensive material, thus making it economically advantageous to reuse the adapters after autoclaving, it is a further advantage that by repeated use of an adapter there is not exerted an unnecessary stress on the legs on the connector of the adapter due to large expansions of the measuring head. The adapter may thus be used more times and last longer.

An adapter that fits within about 2 mm when inserted in an acetabulum will facilitate the work in measuring the diameter of the acetabulum as the doctor does not have to simultaneously hold the measuring head of the adapter in position in the acetabulum so that the rough surface of the measuring head engages the edge of the acetabulum while screwing/turning or displacing the actuation rod.

When the diameter of the metal socket to be inserted in the acetabulum has been determined, a depth gauge may be used for measuring the depth of acetabulum.

The depth gauge may be provided in a through-going opening in the axial direction of the measuring instrument.

In one embodiment, the depth gauge is provided through a central through-going opening in the axial direction of the measuring instrument. The depth gauge may run through the measuring unit, out through the actuation rod and out through the through-going bore of the adapter. Thus, by mounting the depth gauge through the measuring unit, the depth gauge will project at the rear end of the measuring head of the adapter.

By measuring the depth of acetabulum it may be determined how much bone implant (artificial bone mass and/or bone mass taken from the patient) which is to be disposed between acetabulum and metal socket in order that the metal socket is provided a natural and solid bed in acetabulum.

A measuring indication may be indicated on the depth gauge so that, in the relaxed position, a first measuring mark is indicated, after which measuring markings with suitable spacing are indicated. This spacing between the measuring indications will typically indicate one or two millimeters.

The principles described above may also find application in connection with insertion of uncemented prosthesis components in other human joints, e.g. in the marrow cavity of the femur or in the neck of the femur.

Other objectives, features and advantages of measuring adapter will appear from the following detailed disclosure, from the attached claims, as well as from the drawings. It is noted that the measuring adapter relates to all possible combinations of features.

Generally, all terms used in the claims are to be interpreted according to their ordinary meaning in the technical field, unless explicitly defined otherwise herein. All references to "a/an/the [element, device, component, means, step, etc.]" are to be interpreted openly as referring to at least one instance of said element, device, component, means, step, etc., unless explicitly stated otherwise. The steps of any method disclosed herein do not have to be performed in the exact order disclosed, unless explicitly stated.

A spherical cap is the region of a sphere which lies above (or below) a given plane. In other words, a spherical cap is a portion of a sphere cut off by one plane. If the plane passes through the center of the sphere, so that the height of the cap is equal to the radius of the sphere, the spherical cap is called a hemisphere. Alternative terms used instead of spherical cap are spherical dome and spherical segment of one base. If the cap is cut by a second plane, parallel to the first plane, the spherical frustum is called a spherical segment. In other words, a spherical segment is the solid defined by cutting a sphere with a pair of parallel planes. It can be thought of as a spherical cap with the top truncated, and so it corresponds to a spherical frustum.

As used herein, the term "comprising" and variations of that term are not intended to exclude other components, integers, steps or materials.

BRIEF DESCRIPTION OF THE DRAWINGS

By way of example, embodiments of the measuring adapter will now be described with reference to the accompanying drawings, in which:

FIG. 4a is a schematic view of a cross-section of a measuring adapter, wherein the measuring head (2) is in the relaxed state and wherein the measuring head (2) is described by two radiuses r1 and r2;

FIG. 4b is a schematic view of a cross-section of a measuring adapter, wherein the measuring head (2) is described by two radiuses r3 and r4;

DETAILED DESCRIPTION

One embodiment of the measuring adapter will now be described in relation to the figures.

Figure 1B:
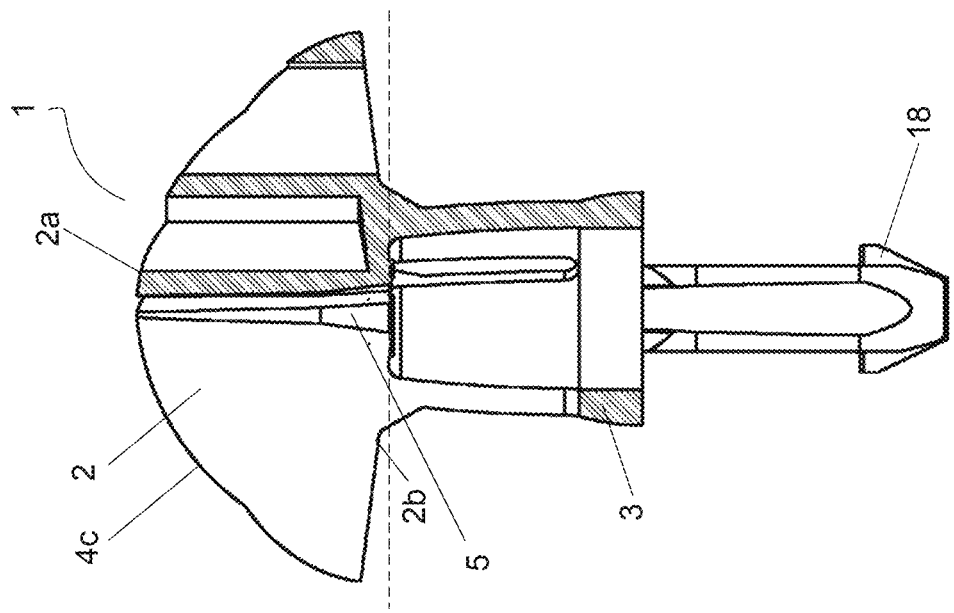
FIG. 1b is a cross sectional view of measuring head of a measuring adapter.
Figure 1A:
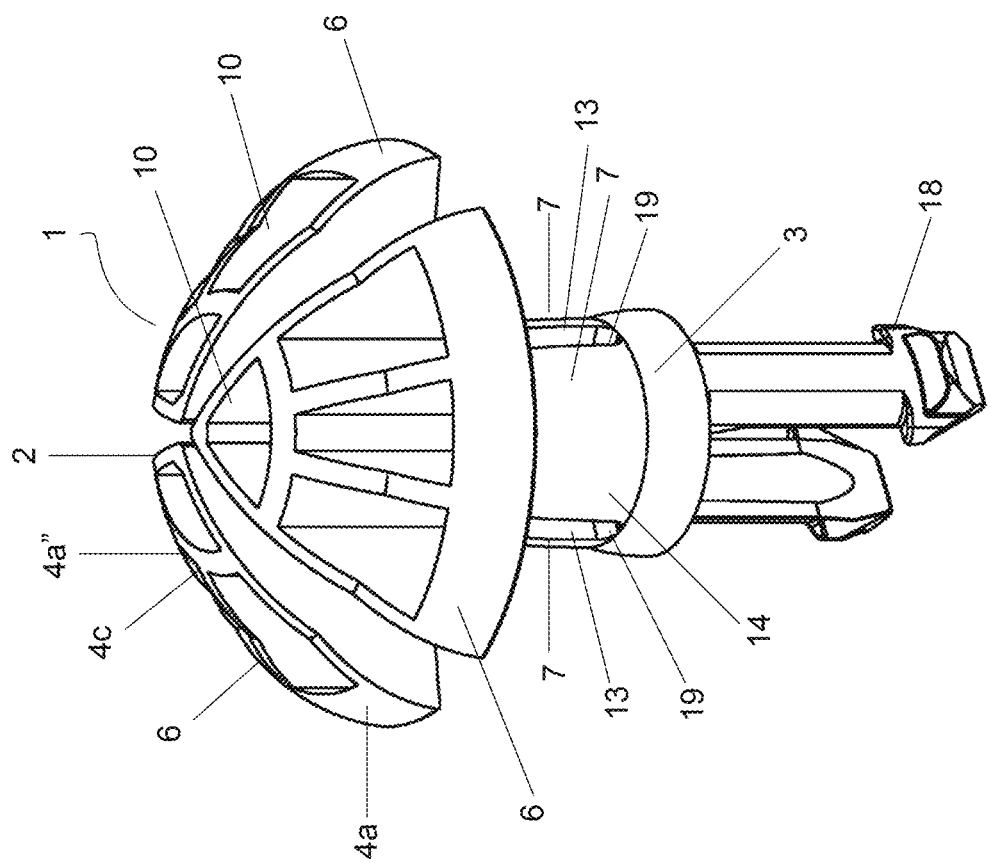
FIG. 1a is a schematic view of a measuring adapter.

FIG. 1a shows the measuring adapter 1 which includes a connector 3 and a measuring head 2 having a surface 4c. In the connector 3 there is shown axially extending slots 13 that divide the end 14 of the connector 3 into a number of legs 7. The slot 13 ends in a circular opening 19 that prevents notch effect in the connector 3 when the measuring head 2 expands.

The measuring head 2 includes a surface 4c which is divided into a number of sections 6 each connected with one of the legs 7 of the connector 3. The surface 4c of the measuring head 2 is divided into two areas with different roughness: bottom part 4a' with rough surface and a top part 4a" with smooth surface. In FIG. 1a the number of legs 7 is three. The number of sections 6 is three.

The measuring head has several through-going holes 10 or windows.

FIG. 1b shows a cross-section in the measuring head 2. Inside the measuring head 2 is provided an axial through-going conical bore 5 which is designed to interact with actuation rod (not shown). In order to bear against and produce some resistance against acetabulum, the surface 4c of the measuring head 2 is divided into a bottom part 4a' with a rough surface and a top part 4a" with a smooth surface.

Figure 2B:
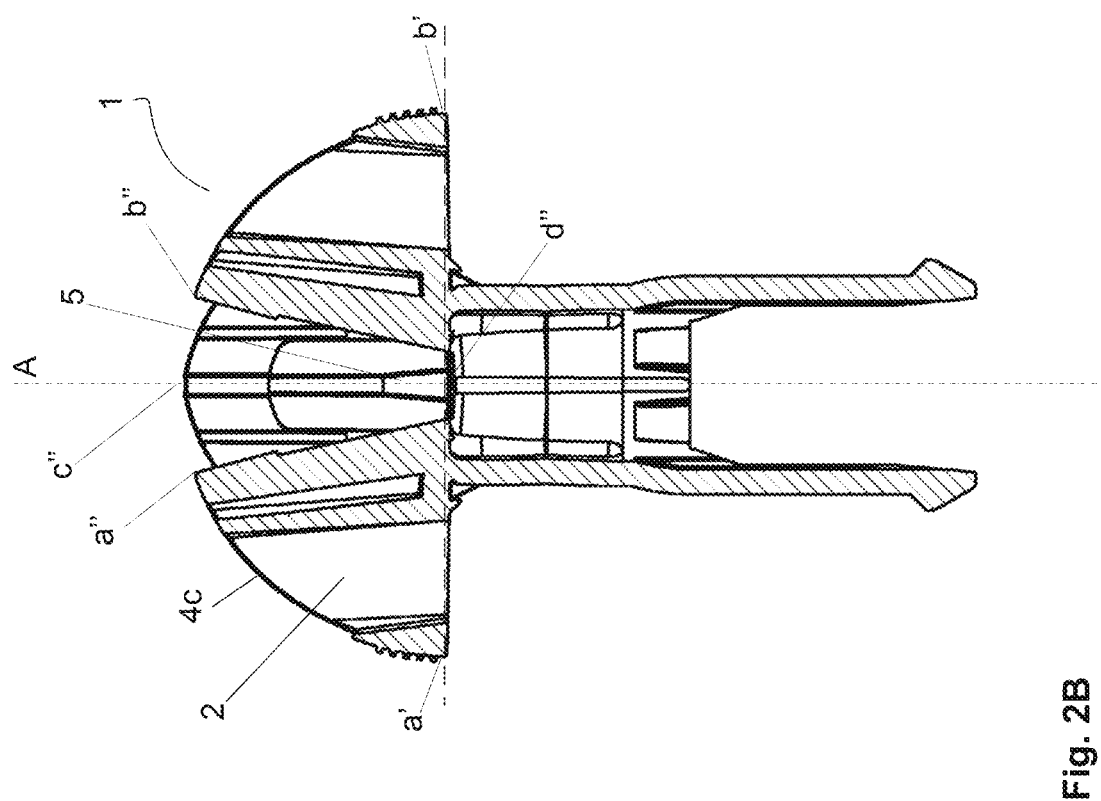
FIG. 2b is a cross sectional view of a measuring adapter, wherein the measuring head in FIG. 2a is in an expanded state.
Figure 2A:
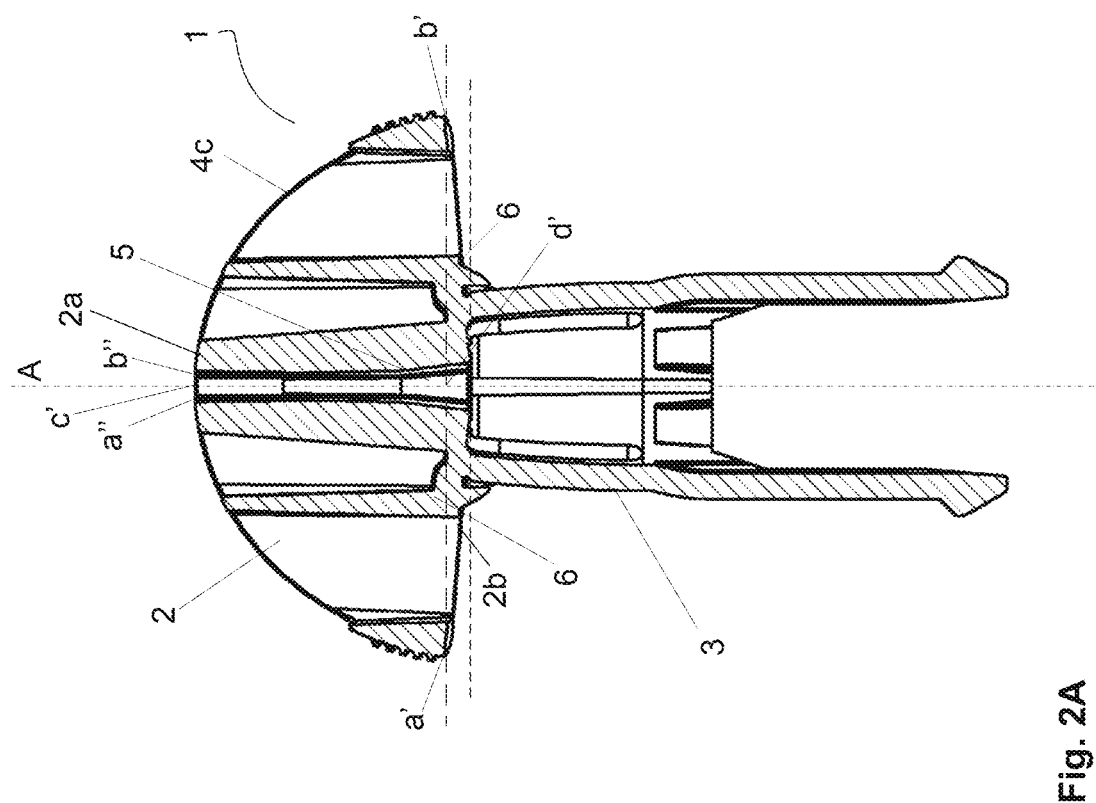
FIG. 2a is a schematic view of a cross-section of measuring adapter, wherein the measuring head (2) in the relaxed state is collapsed compared to a perfect hemisphere.

FIG. 2a is a schematic view of a cross-section of a measuring head 2 of a measuring adapter 1, which, in the relaxed state, is collapsed compared to a perfect hemisphere. The measuring head 2 includes a surface 4c which is divided into a number of sections 6 each connected with one of the legs 7 (not shown) of the connector 3. In the relaxed state shown, the sections 6 are collapsed towards the axis A of the measuring head 2 such that the surface 4c is not hemispherical. Specifically, a curve from a point a' to a point b', through points a", c' and b" is not an arc of a circle. Points a' and b' are located on the outline of the measuring head 2 located on the farthest perpendicular distance from an axis A along the axial direction of the connector 3. Other structures may be located proximal of points a' and b', respectively. Points a" and b" are located on the rim of the central through-going bore 5. Point c' is an imaginary point located on the axis A along the axial direction of the connector 3. A line (a'-b') intersects the axis in a point d'.

FIG. 2b shows the measuring adapter 1 of FIG. 2a in an expanded state, wherein the surface 4c of the measuring head 2 is hemispherical. Specifically, a curve from a point a' to a point b', through points a", b" and c" is an arc of a circle. Points a' and b' are located on the outline of the measuring head 2 located on the farthest perpendicular distance from an axis A along the axial direction of the connector 3. Other structures may be located proximal of points a' and b', respectively. Points a" and b" are located on the rim of the central through-going bore 5. Point c" is an imaginary point located on the axis A along the axial direction of the connector 3. A line (a'-b') intersects the axis in a point d".

Thus, in an expanded state, the curve (a'-a"-c"-b"-b'-d"-a') encloses a hemi circle. Thus, the distances (a'-d"), (d"-b') and (d"-c") are equal.

In some embodiments, in an expanded state, the surface 4c of the measuring head 2 is not hemispherical, but rather a spherical segment, and the curve (a'-a"-c"-b"-b'-d"-a') encloses a circle segment. Thus, the distances (a'-d") and (d"-b') are equal, and the distance (d"-c") is less than the distance (a'-d").

Figure 3B:
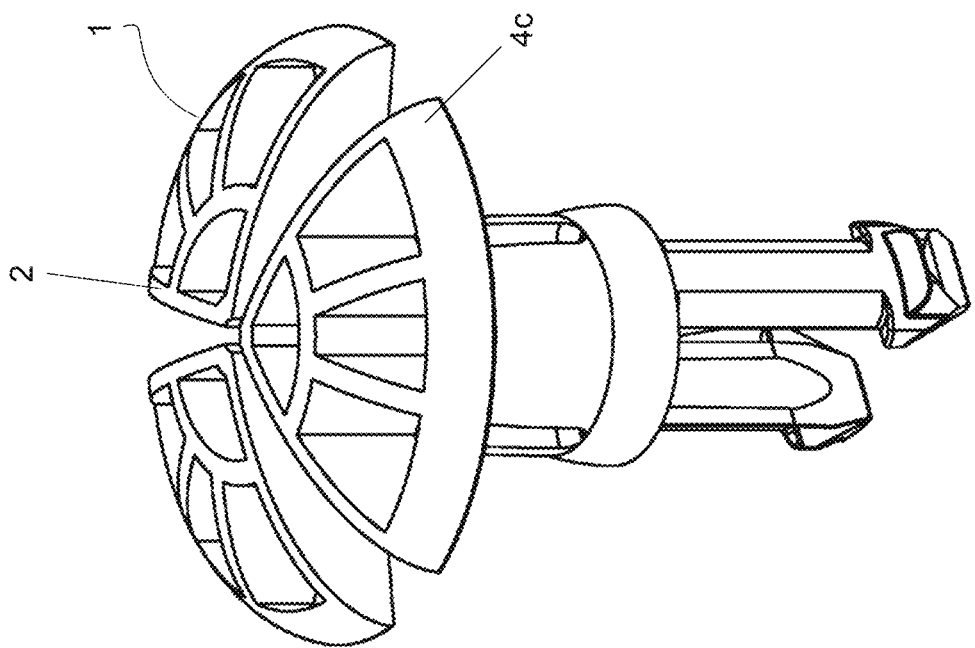
FIG. 3b is a schematic view of a measuring adapter, wherein the measuring head in FIG. 3a is in an expanded state.
Figure 3A:
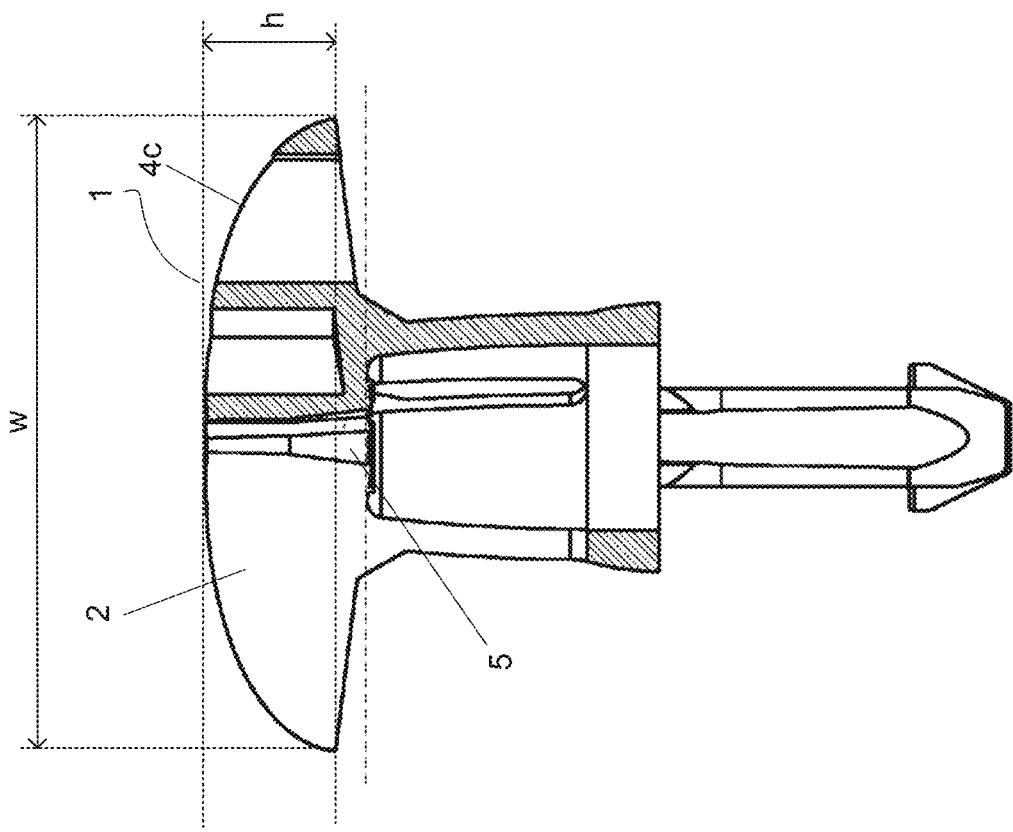
FIG. 3a is a schematic view of cross-section of a measuring adapter, wherein the height (h) of the measuring head (2) is less than half of the ideal width (w) of the measuring head (2)

FIG. 3a is a schematic view of a measuring head 2 of a measuring adapter 1, wherein the height h of the measuring head 2 is less than half of the ideal width w of the measuring head 2. The measuring head 2 has a surface 4c. The measuring head 2 is "flattened", such that the surface 4c is not hemispherical and its cross section resembles an elliptical rather than circular geometry.

FIG. 3b shows the measuring adapter 1 of FIG. 3a in its expanded state, wherein the surface 4c of the measuring head 2 is hemispherical.

FIG. 4a is a schematic view of a cross-section of a measuring head of a measuring adapter 1, wherein the measuring head 2 is described by two radiuses r1 and r2. It is also possible to describe the measuring head 2 by more than two radiuses, such as 3, 4, or 5 radiuses.

FIG. 4b is a schematic view of a cross-section of a measuring head of a measuring adapter 1, wherein the measuring head 2 is described by two radiuses r3 and r4. It is also possible to describe the measuring head 2 by more than two radiuses, such as 3, 4, or 5 radiuses.

Figure 5:
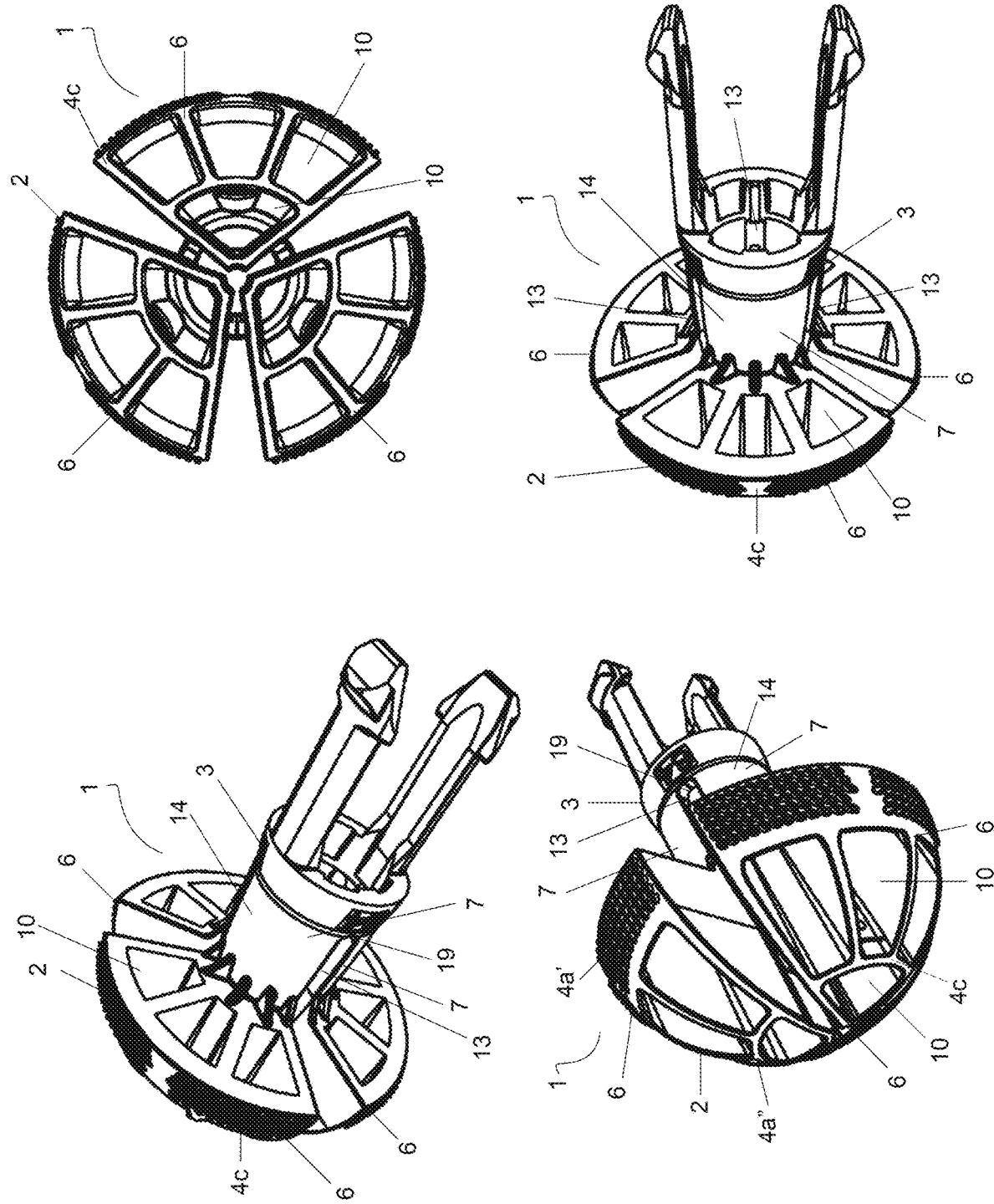
FIG. 5 is a schematic view of a measuring adapter.

FIG. 5 shows schematic views of a measuring head 2 of a measuring adapter 1, wherein the measuring head 2 in the relaxed state is collapsed compared to a perfect hemisphere. The measuring adapter 1 includes a connector 3 and a measuring head 2 having a surface 4c. In the connector 3 there is shown axially extending slots 13 that divide the end 14 of the connector 3 into three legs 7. The slot 13 ends in a circular opening 19 that prevents notch effect in the connector 3 when the measuring head 2 expands.

The measuring head 2 includes a surface 4c which is divided into three sections 6 each connected with one of the legs 7 of the connector 3. The surface 4c of the measuring head 2 is divided into two areas with different roughness: bottom part 4a' with rough surface and a top part 4a" with smooth surface. In the relaxed state shown, the sections 6 are collapsed towards the axis of the measuring head 2 such that the surface 4c is not hemispherical.

The measuring head has several through-going holes 10 or windows.

Figure 6:
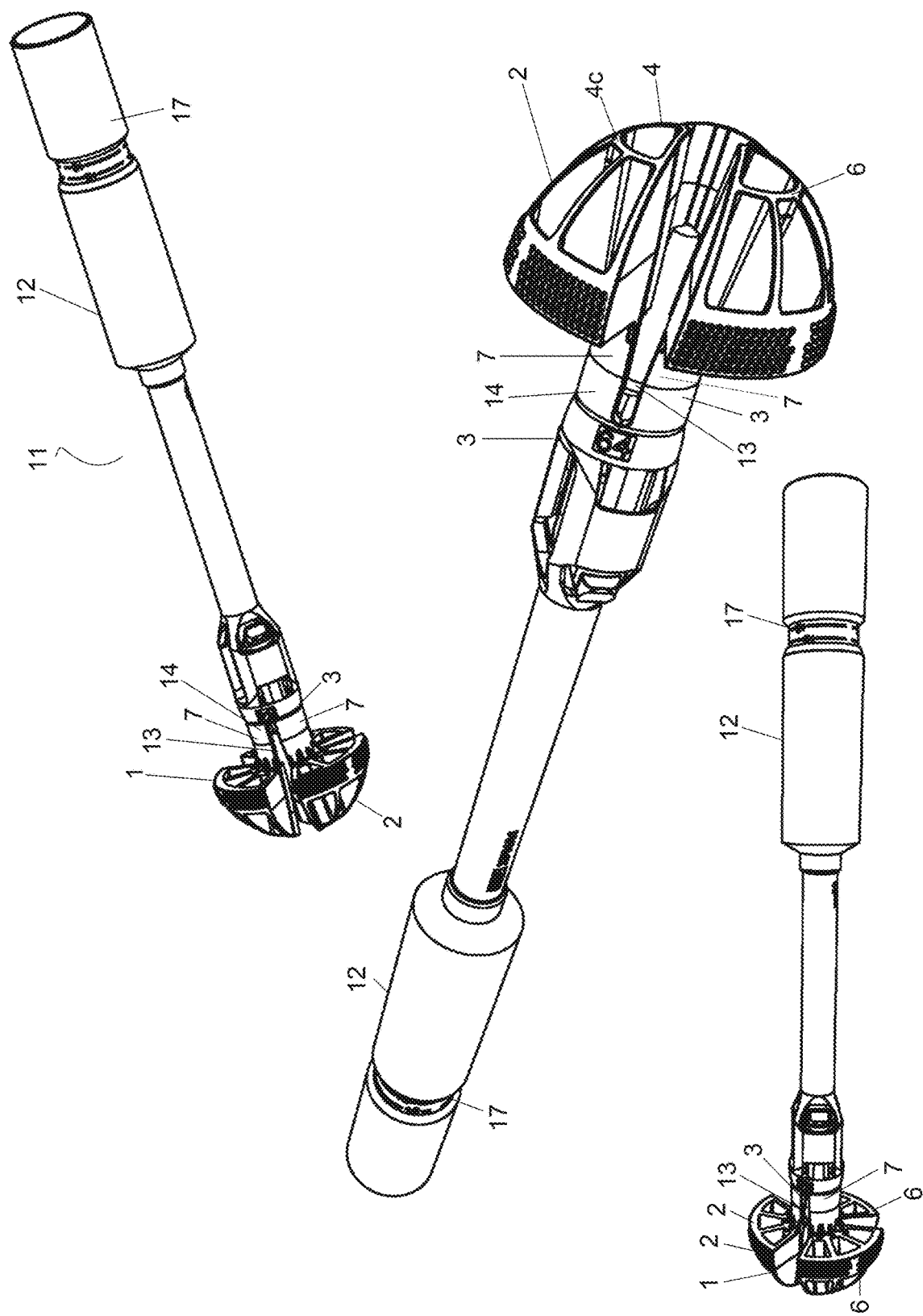
FIG. 6 is a schematic view of a measuring instrument.

FIG. 6 shows a measuring instrument 11 including a measuring adapter 1 and a measuring unit 12.

The measuring adapter 1 includes a connector 3 and a measuring head 2 that has a surface 4c. The connector 3 has at least two axially extending slots 13 dividing the end 14 of the connector 3 into a number of legs 7. The measuring head 2 includes a hemi-spherical surface 4c divided into a number of sections 6 so that each part is connected with one leg 7 of the connector 3. At the end 14 of the connector 3 recesses may be provided, which are designed to interact with corresponding pins (not shown) provided in the securing arrangement (e.g. a mounting ring) of the measuring unit 12. Inside the measuring head 2 is provided an axially through-going conical bore 5 which is designed to interact with the actuation rod 8 of the measuring unit 12.

The measuring unit 12 includes an actuation rod 8, a mounting ring 16 and a millimeter screw device 17. The actuation rod 8 has a conical main part 8a which by axial displacement and engagement with the conical bore 5 in the measuring head 2 forces the separate sections (not shown) of the measuring head 2 from each other. The outward going force caused by the displacement of the actuation rod 8 in relation to the conical opening 8 of the measuring head is absorbed in bending the legs 7 of the connector 3.

The mounting ring 16 may be provided with pins (not shown) which are designed to engage the recesses in the end 14 of the measuring adapter 1.

In order to achieve axial displacement of the actuation rod 8 in relation to the conical opening 8 of the measuring head 2, the measuring unit 12 is provided as a millimeter screw device 17 which by rotation axially displaces the actuation rod 8. Inside the millimeter screw device 17 a releasable ratchet device that ensures tightening of the millimeter screw device 17 may be provided.

Figure 7:
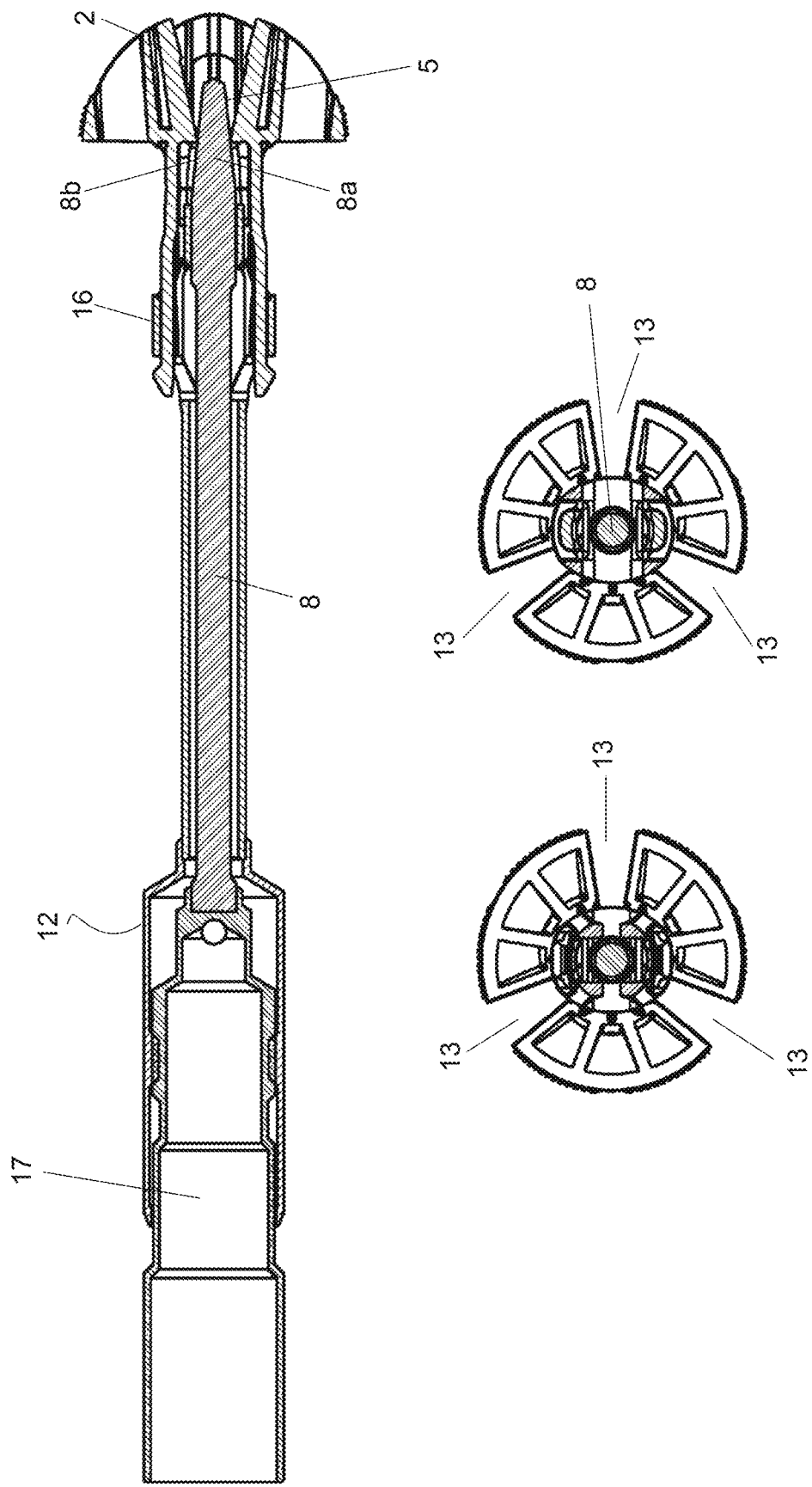
FIG. 7 shows a cross-section of the interaction between measuring head and actuation rod.

FIG. 7 shows a cross-section of the measuring head 2 by actuation of the actuation rod 8, where the conical main part 8*a* of the actuation rod 8 is engaging the conical opening 5 (the through-going bore) of the measuring head 2. An upwards directed axial displacement of the actuation rod 8 will result in the sides of the conical main part 8*a* of the actuation rod 8 forcing the sections 6 of the measuring head from each other, and the slot 13 will be enlarged.

Figure 8C:
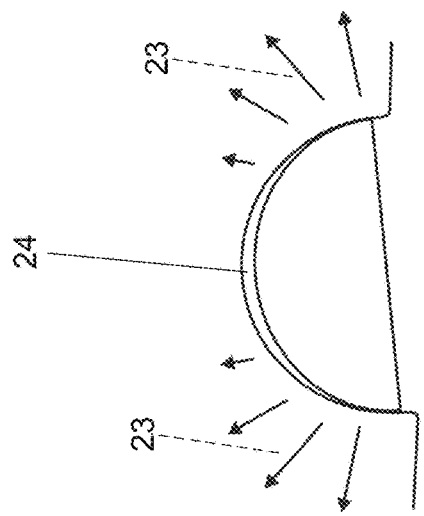
FIGS. 8a-c show views of a metal socket inserted into acetabulum.
Figure 8B:
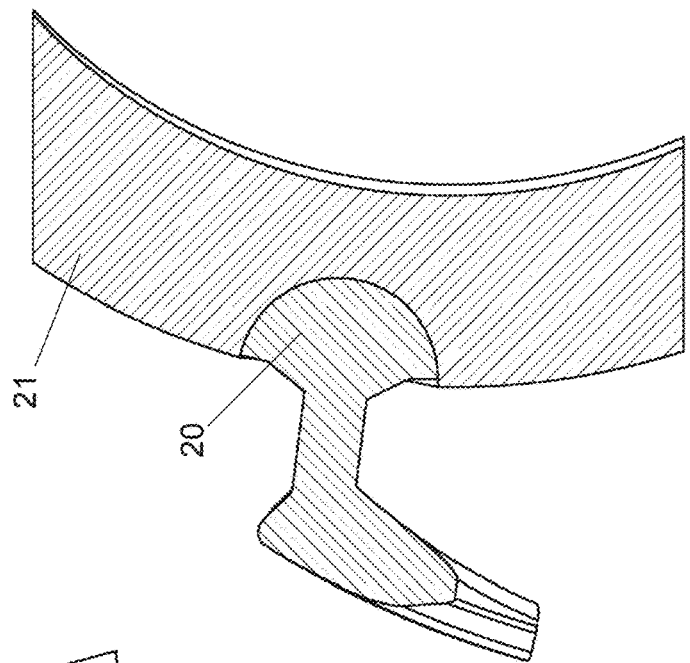
Figure 8A:
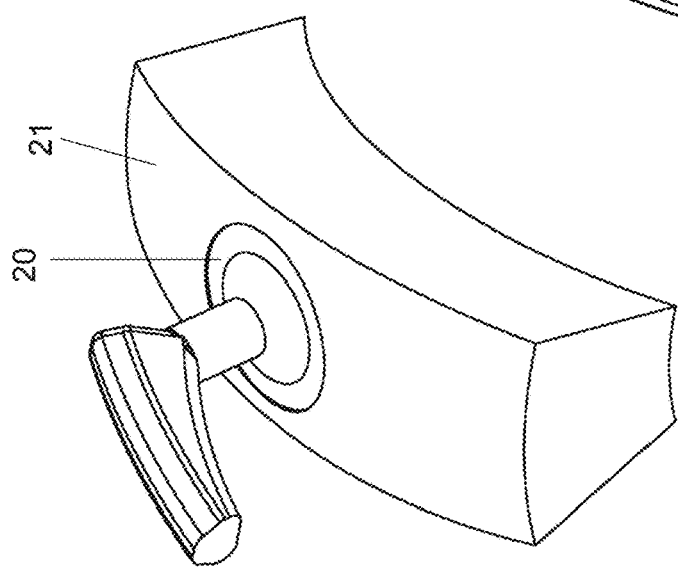

FIG. 8 shows a metal socket 20 inserted in an acetabulum 21. The metal socket 20 is inserted according to the press-fit technique and is oversize compared with acetabulum 21. Therefore, the outwards directed forces 23 will arise, and the metal socket 20 will be securely anchored in the acetabulum. Behind the metal socket 20 an interspace 24 typically appears which is filled with bone mass so that the metal socket 20 is secured in a natural and solid bed in acetabulum 21. It is the depth of this interspace 24 which is measured with the depth gauge (not shown). It is the outwards directed forces 23 that are very necessary in the long run for measuring in order to optimize hip prosthesis operations.

The measuring head 2 according to the embodiments described above may also be provided with pressure sensors evenly distributed on the upper surface 4*a*; the central through-going bore 5, such as the conical through-going bore 5; or in between the upper surface 4*a* and the central through-going bore 5, such as the conical through-going bore 5. The pressure sensors may be piezoceramic pressure sensors. When providing the measuring head 2 with such sensor arrangements, the pressure in acetabulum or the pressure with which the measuring head is pushed into the acetabulum may be measured. In this way a better fit may be accomplished.

It will be appreciated that the measuring adapter has been illustrated with reference to exemplary embodiments, and that the measuring adapter can be varied in many different ways within the scope of the appended claims.

It should also be noted that the inclusion in the appended claims of some of the numerals used in the figures is purely for illustrative purposes and not to be considered as limiting the scope of the claims.

The invention claimed is:

1. A measuring adapter for a measuring instrument for use in connection with hip prosthesis surgery, wherein the measuring adapter comprises:
   a measuring head comprising a front end, a rear end and an upper surface; the measuring head being divided into at least two separate sections; and
   a connector; the connector being hollow and slotted at one end in an axial direction of the measuring head into a number of legs, the number of legs corresponding to the number of the at least two separate sections of the measuring head; wherein each leg of the connector is connected to one of the at least two separate sections of the measuring head on the rear end of the measuring head;
   wherein at least a part of the upper surface of the measuring head is adapted to be moved from a relaxed state to an expanded state,
   wherein in the expanded state the at least a part of upper surface of the measuring head defines an expanded-state perimeter and the at least a part of the upper surface of the measuring head adopts the shape of a spherical cap; or
   a convex shape comprising at least a spherical segment, and
   wherein, in the relaxed state, the at least a part of the upper surface of the measuring head is within the expanded-state perimeter.

2. A measuring adapter according to claim 1, wherein the measuring adapter comprises a bore adapted to receive an actuating rod, wherein the measuring head is adapted to expand from the relaxed state to the expanded state when the actuating rod is displaced in the bore.

3. A measuring adapter according to claim 2, wherein the measuring adapter is connected to a measuring arrangement which is adapted to measure the relative displacement of the actuation rod in relation to a fixed point in the measuring adapter.

4. A measuring adapter according to claim 1, wherein the actuating rod is connected to a computer, and wherein the computer is adapted to control the relative displacement of the actuation rod relative to the measuring head.

5. A measuring adapter according to claim 1, wherein the adapter is connected to a pressure registering unit configured to measure the pressure exerted by the measuring head.

6. A measuring adapter according to claim 5, wherein the pressure registering unit comprises piezo-electric crystals.

7. A measuring adapter according to claim 5, wherein the pressure registering unit is configured to transmit pressure measurements to a computer.

8. The measuring adapter according to claim 1, wherein the measuring head comprises windows, the windows being sized and positioned to allow a user to observe the position of the segments of the measuring head relative to a milled acetabulum in order to observe the size of a milled cavity of the acetabulum.

9. The measuring adapter according to claim 1, wherein the measuring head is divided into at least three separate sections.

10. The measuring adapter according to claim 1, wherein the at least a part of the upper surface of the measuring head comprises a rough surface.

11. The measuring adapter according to claim 1, wherein the upper surface of the measuring head of the measuring adapter comprises a rough surface at a lower part of the upper surface and a smooth surface on an upper part of the upper surface.

12. The measuring adapter according to claim 1, wherein the connector comprises a securing arrangement provided at an opposite end of the connector relative to a connection to the measuring head.

13. The measuring adapter according to claim 12, wherein the securing arrangement comprises at least one recess for a bayonet socket.

14. The measuring adapter according to claim 1, wherein the measuring adapter is made of a hard yet flexible material, wherein the material is chosen from the group consisting of a metal alloy, a plastic material, a plastic composite, a ceramic material and combinations thereof.

15. A measuring instrument comprising
    a measuring adapter according to claim 1 and
    a measuring unit comprising:
      an actuating rod adapted to be received by a bore of the measuring adapter, wherein a main part of the actuating rod is adapted to interact displaceably with the bore of the measuring adapter and thereby change the diameter of the measuring head, and
      a handle means, wherein in connection with the handle means, means for displacement of the actuation rod and registration of the relative displacement of the actuation rod relative to the measuring head is provided.

16. A measuring adapter for a measuring instrument for use in connection with hip prosthesis surgery, wherein
the measuring adapter comprises a measuring head and a connector;
the measuring head comprises a front end, a rear end and an upper surface; wherein
the upper surface is convex;
the measuring head is adapted to expand from a relaxed state to an expanded state; and
the measuring head is divided into at least two separate sections;
the connector is hollow and slotted at one end in an axial direction of the measuring head to define a number of legs, the number of legs corresponding to the number of the at least two separate sections of the measuring head; wherein
the legs of the connector are each connected to one of the at least two separate sections of the measuring head on the rear end of the measuring head; and
the measuring head comprises windows, the windows being sized and positioned to allow a user to observe the position of the segments of the measuring head relative to a milled acetabulum in order to observe the size of a milled cavity of the acetabulum.

17. A measuring instrument comprising
a measuring adapter according to claim 16 and
a measuring unit comprising
an actuating rod adapted to be received by a bore of the measuring adapter, wherein a main part of the actuating rod is adapted to interact displaceably with the bore of the measuring adapter and thereby change the diameter of the measuring head, and
a handle means, wherein in connection with the handle means, means for displacement of the actuation rod and registration of the relative displacement of the actuation rod relative to the measuring head is provided.

* * * * *